(12) United States Patent
Takayanagi (10) Patent No.: US 11,317,845 B2
(45) Date of Patent: May 3, 2022

(54) PHYSIOLOGICAL INFORMATION WAVEFORM PROCESSING METHOD, PROGRAM, COMPUTER READABLE STORAGE MEDIUM, AND PHYSIOLOGICAL INFORMATION WAVEFORM PROCESSING APPARATUS

(71) Applicant: NIHON KOHDEN CORPORATION, Tokyo (JP)

(72) Inventor: Tsuneo Takayanagi, Tokorozawa (JP)

(73) Assignee: NIHON KODHEN CORPORATION, Tokyo (JP)

( * ) Notice: Subject to any disclaimer, the term of this patent is extended or adjusted under 35 U.S.C. 154(b) by 136 days.

(21) Appl. No.: 16/494,952

(22) PCT Filed: Apr. 5, 2018

(86) PCT No.: PCT/JP2018/014629
§ 371 (c)(1),
(2) Date: Sep. 17, 2019

(87) PCT Pub. No.: WO2018/193867
PCT Pub. Date: Oct. 25, 2018

(65) Prior Publication Data
US 2020/0029846 A1 Jan. 30, 2020

(30) Foreign Application Priority Data

Apr. 19, 2017 (JP) .............................. JP2017-082921

(51) Int. Cl.
*A61B 5/00* (2006.01)
*A61B 5/349* (2021.01)

(52) U.S. Cl.
CPC ............ *A61B 5/349* (2021.01); *A61B 5/7221* (2013.01); *A61B 5/7264* (2013.01)

(58) Field of Classification Search
CPC ...... A61B 5/349; A61B 5/7221; A61B 5/7264
USPC ......................................................... 600/509
See application file for complete search history.

(56) References Cited

U.S. PATENT DOCUMENTS

| 2014/0194764 A1* | 7/2014 | Takayanagi .......... A61B 5/7221 600/517 |
| 2016/0114169 A1* | 4/2016 | Sheldon ............... A61N 1/3702 607/17 |
| 2016/0144190 A1* | 5/2016 | Cao ..................... A61N 1/36585 607/17 |

FOREIGN PATENT DOCUMENTS

JP 2017-042388 A 3/2017

OTHER PUBLICATIONS

Vijaya et al. "ANN-based ORS-complex analysis of ECG", Journal of Medical Engineering & Technology, vol. 22, No. 4, Jan. 9, 1998 (Jan. 9, 1998), pp. 160-167 (Year: 1998).*
International Search Report Issued in Patent Application No. PCT/JP2018/014629 dated Dec. 7, 2018.

(Continued)

*Primary Examiner* — Erin M Piateski
(74) *Attorney, Agent, or Firm* — Pearne & Gordon LLP (57) ABSTRACT

A method is implemented by a computer, and includes: (a) acquiring at least one set of waveform data having a time duration from physiological information waveform data; (b) classifying a waveform included in the waveform data into a predetermined type of waveform; (c) determining validity of a classification result of the waveform; and (d) correcting the classification result in accordance with the validity of the classification result.

7 Claims, 4 Drawing Sheets

(56) References Cited

OTHER PUBLICATIONS

Written Opinion Issued in Patent Application No. PCT/JP2018/014629 dated Dec. 7, 2018.
Maglaveras, Nicos, et al., "ECG pattern recognition and classification using non-linear transformations and neural networks: A Review", International Journal of Medical Informatics, Elsevier Scientific Publishers, Shannon, IR, vol. 52, No. 1-3, (1998), pp. 1191-1208.
Mehta, S. S., et al., "Detection of P and T-waves in Electrocardiogram", Proceedings of the World Congress on Engineering and Computer Science, 2008 WCECS 2008, Oct. 22-24, 2008, San Francisco, USA.
Vijaya, G., et al., "ANN-based QRS-complex analysis of ECG", Journal of Medical Engineering & Technology, vol. 22, No. 4, Jan. 9, 1988, pp. 160-167.
Dohare, Ashok, et al., "An efficient new method for the detection of QRS in electrocardiogram", Computers and Electrical Engineering, vol. 40, No. 5, (Jul. 2014), pp. 1717-173.
Maglaveras, Nicos, et al., "ECG pattern recognition and classification using non-linear transformations and neural networks: A Review", International Journal of Medical Informatics, Elsevier Scientific Publishers, Shannon, IR, vol. 52, No. 1-3, (1998), pp. 191-208. Page numbers corrected for previously-cited reference.
Dohare, Ashok, et al., "An efficient new method for the detection of QRS in electrocardiogram", Computers and Electrical Engineering, vol. 40, No. 5, (Jul. 2014), pp. 1717-1730. Page numbers corrected for previously-cited reference.

\* cited by examiner

PHYSIOLOGICAL INFORMATION WAVEFORM PROCESSING METHOD, PROGRAM, COMPUTER READABLE STORAGE MEDIUM, AND PHYSIOLOGICAL INFORMATION WAVEFORM PROCESSING APPARATUS

TECHNICAL FIELD

The present disclosure relates to a physiological information waveform processing method, a program, a computer readable storage medium storing the program, and a physiological information waveform processing apparatus.

BACKGROUND ART

The following disclosure has been made in JP-A-2017-42388. That is, a time difference as to an electrocardiogram (ECG) waveform is calculated from sampling data. An index value is calculated from a calculation result of the time difference. Based on the index value, determination is made as to which waveform the sampling data belong to.

In JP-A-2017-42388, of a measured waveform, a narrow segment used for each sampling is set as a subject to be determined. For this reason, different waveforms such as a T wave and a QRS complex may be classified into the same waveform when there is a high degree of similarity between narrow segments of the two waveforms in the vicinity of the sampling. Therefore, there is still room for improvement in order to classify the waveform accurately.

SUMMARY OF INVENTION

The present disclosure provides a physiological information waveform processing method:

capable of improving recognition accuracy of a waveform. The present disclosure also provides a program, a storage medium storing the program, and a physiological information waveform processing apparatus, which is capable of improving recognition accuracy of a waveform.

According to one or more aspects of the present disclosure, there is provided a method implemented by a computer, which comprises:

(a) acquiring at least one set of waveform data having a time duration from physiological information waveform data;

(b) classifying a waveform included in the waveform data into a predetermined type of waveform;

(c) determining validity of a classification result of the waveform; and (d) correcting the classification result in accordance with the validity of the classification result.

According to one or more aspects of the present disclosure, there is provided the program causing a computer to perform the method.

According to one or more aspects of the present disclosure, there is provided a computer-readable storage medium storing the program.

According to one or more aspects of the present disclosure, there is provided an apparatus, which comprises:

at least one processor; and a memory storing a computer-readable instruction, wherein the computer-readable command, when executed by the processor, causes the processor to perform the method.

DESCRIPTION OF EMBODIMENTS

A physiological information waveform processing method, a storage medium, a program and a physiological information waveform processing apparatus according to an embodiment of the present disclosure will be described below by way of example with reference to the drawings.

<Physiological Information Waveform Processing Apparatus>

Figure 1:
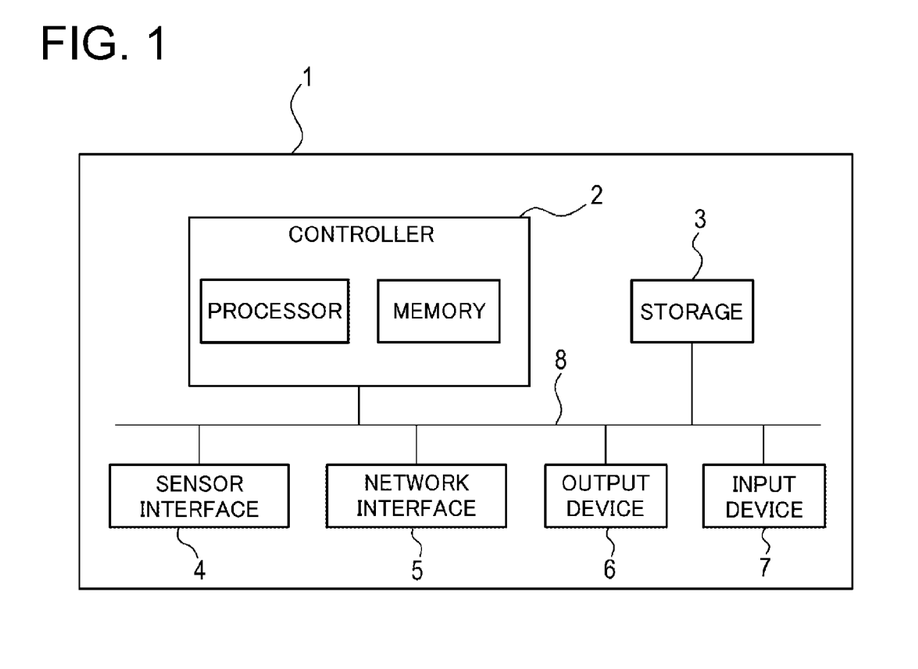
FIG. 1 is a configuration diagram illustrating a physiological information waveform processing apparatus according to an embodiment of the present disclosure.

As shown in FIG. 1, the physiological information waveform processing apparatus 1 includes a controller 2, a storage 3, a sensor interface 4, a network interface 5, an output device 6, and an input device 7, which are connected to one another communicably through a bus 8.

The physiological information waveform processing apparatus 1 is an apparatus for processing physiological information waveform data. As an example, the physiological information waveform data are electrocardiogram (ECG) waveform data (ECG data) in an ECG. The physiological information waveform processing apparatus 1 may be an electrocardiographic monitor, a personal computer, a smartphone, or a wearable device such as an Apple Watch.

As shown in FIG. 1, the controller 2 includes a memory and a processor. For example, the memory may include an ROM (Read Only Memory) in which various programs etc. have been stored, an RAM (Random Access Memory) having a plurality of work areas in which the various programs etc. to be executed by the processor can be stored, etc. For example, the processor may be a CPU (Central Processing Unit) which is configured to expand a designated program from the various programs which have been stored in the ROM, onto the RAM, and execute various processes in cooperation with the RAM.

When the processor expands a physiological information waveform processing program which will be described later, onto the RAM, and executes the physiological information waveform processing program in cooperation with the RAM, the controller 2 may control various operations of the physiological information waveform processing apparatus 1. Details of the controller 2 and the physiological information waveform processing program will be described later.

The storage 3 may be a storage device such as an HDD (Hard Disk Drive), an SSD (Solid Stage Drive) or a flash memory, which is configured to store programs or various data. The physiological information waveform processing program may be installed into the storage 3.

ECG data acquired by a not-shown ECG sensor may be stored into the memory of the controller 2 or the storage 3. The ECG sensor is configured to measure a weak electric signal generated from a heart of a patient to thereby acquire ECG data. Here, the ECG data represents an ECG waveform having waveforms (P waves, QRS complexes, etc.) occurring continuously on a time axis.

The sensor interface 4 is configured to connect the physiological information waveform processing apparatus 1 to the ECG sensor communicably. For example, the ECG data acquired by the ECG sensor can be transmitted to the controller 2 or the storage 3 through the sensor interface 4. The sensor interface 4 may have an A/D conversion function.

The network interface 5 is configured to connect the physiological information waveform processing apparatus 1 to a not-shown communication network. Here, the communication network may include at least one of an LAN (Local Area Network), a WAN (Wide Area Network), and the Internet etc. For example, a processed result outputted from the controller 2 may be transmitted to another computer disposed on the communication network through the network interface 5.

The output device 6 may be a display device which display the processed result etc. of the controller 2 thereon. The display device is, for example, a liquid crystal display or an organic EL display or the like. The output device 6 may be also a printer device such as an inkjet printer or a laser printer. For example, the processed result outputted from the controller 2 may be displayed on a display screen of the display device or printed by the printer.

The input device 7 is configured to receive an input operation from an operator operating the physiological information waveform processing apparatus 1, and output an operating signal in response to the input operation. For example, the input device 7 is a touch panel superimposed and disposed on the display device of the output device 6, an operation button installed in a housing, a mouse, a keyboard, etc.

Figure 2:
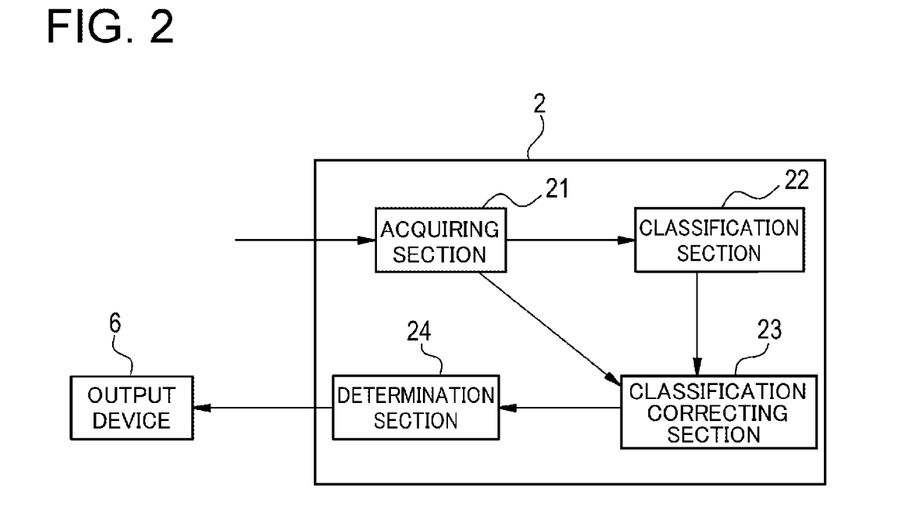
FIG. 2 illustrates illustrating a functional block of a controller.

FIG. 2 is a diagram illustrating a functional block of the controller 2 of the physiological information waveform processing apparatus 1 shown in FIG. 1. As shown in FIG. 2, the controller 2 includes an acquiring section 21, a classification section 22, a classification correcting section 23, and a determination section 24.

Figure 3:
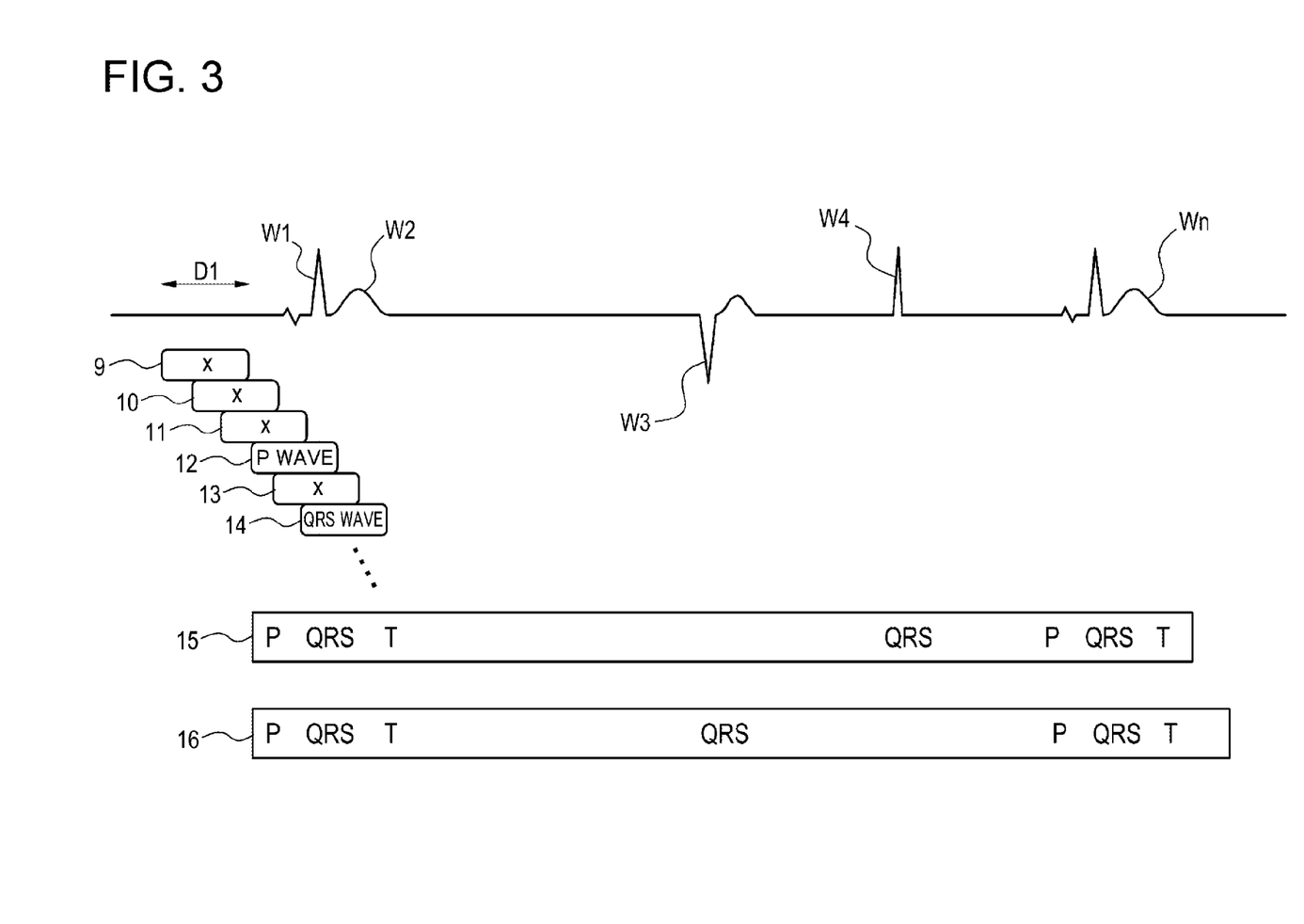
FIG. 3 is an explanatory view illustrating an overview of processing in the present disclosure.

The acquiring section 21 acquires waveform data of a predetermined time duration from a measured physiological information waveform (e.g. ECG data) on a time axis. The predetermined time duration is a time duration which serves as a processing unit of the physiological information waveform. For example, the predetermined time duration can be set as a time duration (100 ms to 1 S) corresponding to one waveform or one PP interval on the time axis of the measured physiological information waveform. As a preferable example, the predetermined time duration is 160 ms. In FIG. 3, D1 represents the predetermined time duration in the physiological information waveform.

A plurality of predetermined time duration for acquiring waveforms may be set on the time axis of the measured physiological information waveform. In addition, the plurality of time duration may be set to at least partially overlap with one another on the time axis. As an example in which the plurality of time duration are set to partially overlap with one another on the time axis, sets of waveform data 9 to 14 are shown in FIG. 3. The sets of waveform data 9 to 14 are acquired with a plurality of time duration which are set so that adjacent anterior and posterior ones of the time duration partially overlap with each other. Each of the predetermined time duration may be set to at least 50% overlap with another anterior or posterior time duration on the time axis. When the t duration are set to about 50% overlap with one another, a resolution of the physiological information waveform processing can be increased and recognition accuracy of the physiological information waveform can be improved more greatly. In addition, the plurality of time duration may be one fixed time duration, or different time duration from one another.

The classification section 22 may be constructed based on machine learning about the physiological information waveform. As an example, the classification section 22 may be constructed based on deep learning about big data of the physiological information waveform using a multilayered neural network (NN).

The classification section 22 is configured to classify a waveform included in the waveform data of the predetermined time duration acquired by the acquiring section 21, into a predetermined type of waveform. Examples of the predetermined type of waveform include a P wave, a QRS complex, a T wave, etc. included in an ECG. A classification result of the classification section 22 is stored into the memory of the controller 2 or the storage 3.

The classification correcting section 23 is configured to determine validity of the classification result classified by the classification section 22. Here, the validity of the classification result means whether the classification result is conformed to (valid for) the physiological information waveform on the time axis or not. For example, the validity of the classification result is determined based on whether or not the physiological information waveform on the time axis satisfies various thresholds or various criteria such as whether to conform to the shape of the predetermined type of waveform or not, whether to be high or low in amplitude, whether to be long or short in width, whether to be larger or smaller than each threshold, etc. The various thresholds and the various criteria about the validity are stored in the memory of the controller 2 or the storage 3.

In addition, the classification correcting section 23 is configured to correct the classification result in accordance with the determined validity of the classification result. Here, correction of the classification result in accordance with the determined validity is performed in the following manner. That is, when the validity of the classification result is high, the classification result is not corrected. On the other hand, when the validity of the classification result is low, the classification result is corrected. Details about determination of the validity of the classification result will be described later.

The determination section 24 is configured to acquire the classification result of the classification section 22 whose validity has been determined as high by the classification correcting section 23, and the classification result of the classification section 22 whose validity has been determined as low and which has been corrected by the classification correcting section 23, and make various determinations. As an example, the determination section 24 acquires the classification result of the classification section 22 whose validity as P wave has been determined as high and the classification result of the classification section 22 whose validity as P wave has been determined as low and which has been corrected by the classification correcting section 23, and determines occurrence of an atrioventricular block.

Next, an overview of the physiological information waveform processing method will be described below with reference to FIG. 3. FIG. 3 is an explanatory view illustrating an overview of the processing in the present disclosure.

From measured ECG data W on a time axis, the acquiring section 21 acquires waveform data sets 9 to 14, . . . , and N each having a predetermined time duration D1 in the ECG data (acquisition step). Incidentally, the whole of the ECG data is indicated as a waveform W, and individual waveforms are indicated as W1, W2, . . . , and Wn (n is an integer of one or more).

The classification section 22 classifies each of the waveform data sets 9 to 14, . . . , and N acquired by the acquiring section 21, into a predetermined type of waveform (P wave) (classification step). As a classification result 15 of waveform classification process performed by the classification section 22, "each of the waveform data sets 9 to 11 indicates none of P wave, QRS complex and T wave (noise)", "the waveform data set 12 indicates P wave", "the waveform data set 13 indicates none of P wave, QRS complex and T wave (noise)" and "the waveform data set 14 indicates QRS complex" are shown in FIG. 3.

The classification correcting section 23 determines validity of the classification result 15 classified by the classification section 22, and corrects the classification result 15 in accordance with the determined validity (correction step).

In the example shown in FIG. 3, the classification correcting section 23 determines that the waveform data set 14 including the waveform W1 is "QRS complex", determines that validity of the classification "QRS complex" of the waveform data set 14 of the classification result 15 is high, and maintains the classification result 15 of the waveform data set 14. A classification result 16 in FIG. 3 illustrates that the classification "QRS complex" of the waveform data set 14 including the waveform W1 is maintained.

In the example of FIG. 3, the classification correcting section 23 determines that a waveform data set including a waveform W4 does not indicate "QRS complex", determines that validity of the classification "QRS complex" of the waveform data set including the waveform W4 in the classification result 15 is low, and corrects the classification result 15. By this correction, an RR interval, a PP interval (waveform interval) or the like in the ECG data W is changed, and a period (waveform interval) of the predetermined type of waveform such as the QRS complex is also updated. The classification correcting section 23 determines the validity of the classification result 15 again based on the updated period etc. (waveform interval).

In FIG. 3, in case where the classification result of the waveform data set of the time duration including the waveform W4 is corrected such that the waveform data does not indicate "QRS complex", the RR interval on the time axis is changed and the period of the QRS complex is changed. The classification correcting section 23 checks characteristics of a waveform of a waveform data set of a time duration nearby a time on the time axis where presence of a QRS complex is estimated, based on the changed RR interval and the changed period of the QRS complex. In the example, the classification correcting section 23 determines that a waveform data set including a waveform W3 satisfies all characteristics of the QRS complex, and determines that validity of the classification result 15 "none of P wave, QRS complex and T wave (noise)" for the waveform data set including the waveform W3 is low, and corrects the classification result 15. The classification result 16 in FIG. 3 shows that the classification of the waveform data set including the waveform W3 has been corrected to "QRS complex". The classification result which has been corrected in accordance with the determination of the validity by the classification correcting section 23 is stored into the memory of the controller 2 or the storage 3.

Figure 4:
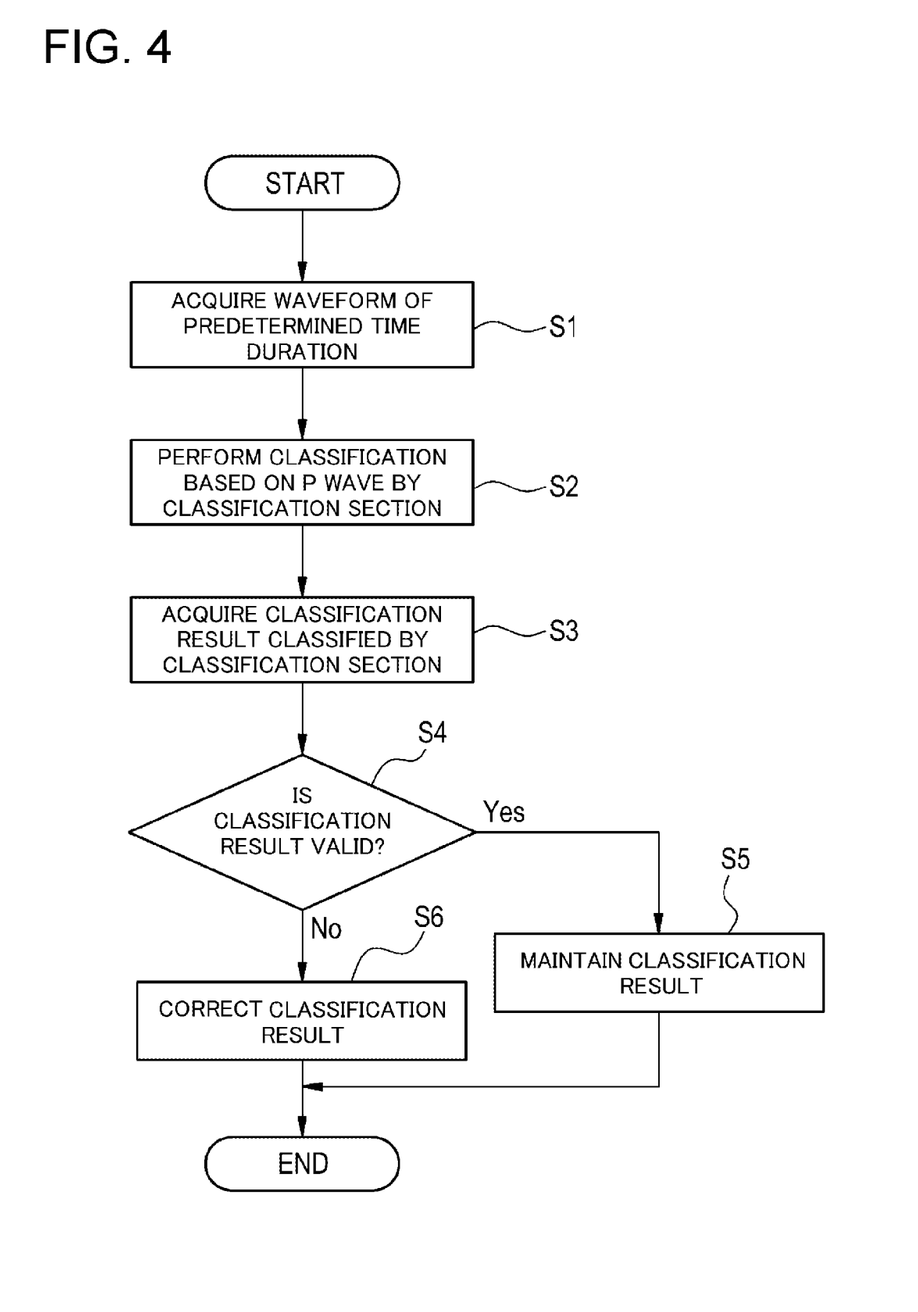
FIG. 4 illustrates a flow chart of a physiological information waveform processing method according to the embodiment.
Figure 5:
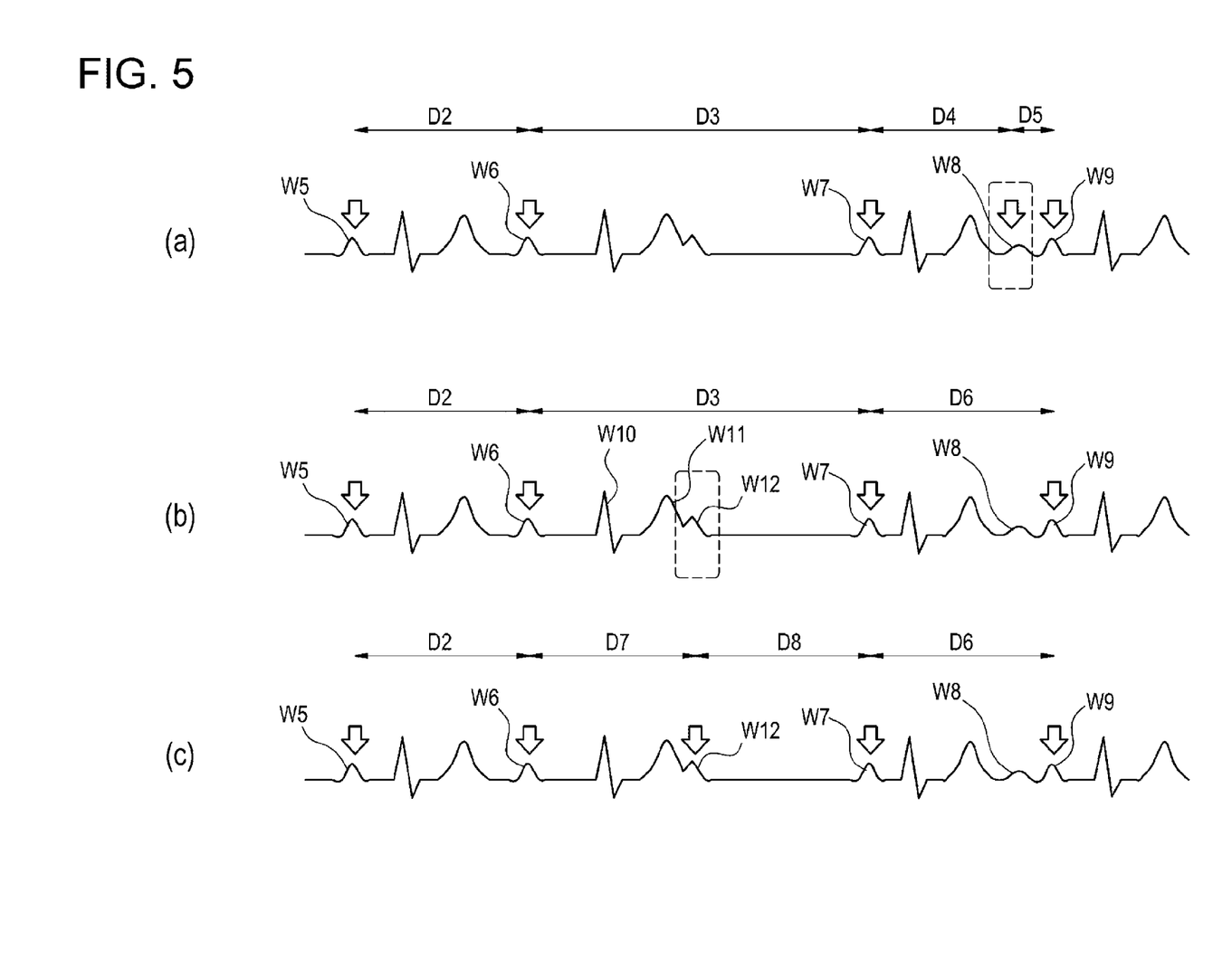
FIG. 5 are views explaining a classification result of a waveform (P wave) included in a predetermined time duration and a correction method of the classification result.

Next, an example of the physiological information waveform processing method for performing classification of the P wave as the type of waveform will be described in more detail with reference to FIG. 4 and FIG. 5. FIG. 4 is a view illustrating a flow chart of the physiological information waveform processing method according to the embodiment. FIG. 5 are views for explaining a waveform classification result (P wave) and a correction method of the classification result. More specifically, (a) of FIG. 5 is a view illustrating the P wave classification result classified by the classification section 22. (b) and (c) of FIG. 5 are views illustrating classification results corrected by the classification correcting section 23. In FIG. 5, waveforms classified into P waves are designated by down arrows respectively.

First, the acquiring section 21 of the physiological information waveform processing apparatus 1 acquires waveform data sets 1 to N of predetermined time duration from measured ECG data W on a time axis (acquisition step designated by S1 in FIG. 4).

Next, the classification section 22 classifies the waveform data sets 1 to N acquired by the acquiring section 21 into P waves each of which is a predetermined type of waveform (classification step designated by S2 in FIG. 4). (a) of FIG. 5 illustrates a classification result that waveform data sets including waveforms W5. W6, W7, W8 and W9 respectively are classified into P waves by the classification section 22.

Next, the classification correcting section 23 acquires the classification result classified by the classification section 22 (S3 in FIG. 4). In addition, the classification correcting section 23 acquires the ECG data W from the acquiring section 21 in order to determine validity. The classification correcting section 23 determines the validity of the classification result for the waveform data sets 1 to N classified by the classification section 22 (S4).

<When Validity is High>

When the validity of the classification result of the classification section 22 is high (YES in S4), the classification correcting section 23 maintains the classification result of the classification section 22 (S5). In the example, the classification correcting section 23 determines that the validity of the classification "P wave" of each of the waveform data sets including the waveforms W5, W6, W7 and W9 is high (YES in S4). Based on this determination, the classification "P wave" of the waveform data set including the waveform W5, W6, W7, W9 is maintained, as shown in (b) of FIG. 5 (S5 in FIG. 4).

<When Validity is Low>

When it is determined that the validity of the classification result is low (NO in S4), the classification correcting section 23 corrects the classification result (S6). The correction (S6) of the classification result can be determined in accordance with the waveform type.

As an example of the correction processing in S4 to S6 of FIG. 4, correction processing (a first correction step, a second correction step and a third correction step) in waveform classification based on P wave will be described.

<First Correction Step>

In the first correction step, the classification correcting section 23 performs correction to reclassify a waveform which is not P wave. In the first correction step, at least one of the following three corrections is carried out in order to perform the correction to reclassify the waveform which is not P wave.

Correction (1): It is determined whether a waveform included in each of waveform data set each having a predetermined time duration is P wave or noise (none of P wave, QRS complex and T wave), and correction is performed to change classification "P wave" of the waveform data set which has been thus determined as not P wave, to not "P wave".

Correction (2): A plurality of waveforms included in the waveform data sets of the predetermined time duration are classified into a group with reference to commonality of the plurality of waveforms, it is determined whether one of the waveforms included in the group is P wave or not, and correction is performed to reclassify the determination result of the one waveform as a determination result of all the waveform data sets included in the group.

Correction (3): It is determined whether the waveform included in each of the waveform data sets of the predetermined time duration is P wave or another wave (QRS complex or T wave) than the P wave, and correction is performed to change the classification "P wave" to not "P wave" when the waveform has been determined as the other wave (the QRS complex or the T wave) than the P wave.

In (a) of FIG. 5, a waveform data set including a waveform W8 is classified into "P wave" by the classification section 22. In the first correction step, the classification correcting section 23 determines that the waveform data set including the waveform W8 is "noise" (none of P wave, QRS complex and T wave), determines that validity of the classification result is low (NO in S4 of FIG. 4), and corrects the classification (S6). (b) of FIG. 5 illustrates that the classification of the waveform data set including the waveform W8 has been corrected to "not P wave (noise)" by the classification correcting section 23.

When the classification is corrected to "not P wave" by the first correction step, PP intervals, which are time duration (waveform intervals) about the ECG data W, are changed and P wave periods (waveform intervals) are also changed. The PP intervals which have not been corrected by the first correction step are D2, D3, D4 and D5, as shown in (a) of FIG. 5. However, the PP intervals, which have been corrected by the first correction step, are changed to D2, D3 and D6, as shown in (b) of FIG. 5.

<Second Correction Step>

Since the waveform intervals have been changed by the first correction step, the classification correcting section 23 determines validity of the classification result again based on the waveform intervals (the PP intervals, the P wave periods) which have been changed by the processing by the first correction step, and executes the second correction step to correct the classification result in accordance with the validity (S4 to S6 in FIG. 4). Since details of the determination of the validity of the second correction step are similar to or the same as those of the first correction step, the description thereof will be omitted.

<Third Correction Step>

After the first correction step and the second correction step, the classification correcting section 23 executes the third correction step to supplement an omission of classification "P wave" which should have been classified by the classification section 22 (S4 to S6 in FIG. 4). The supplementation of the omission of the classification "P wave" is determined based on the P wave periods etc. (waveform intervals) which have been changed by the first correction step and the second correction step.

The classification correcting section 23 acquires the classification result which has been corrected by the first correction step and the second correction step, and acquires the PP intervals and the P wave periods (waveform intervals) which have been changed by the first correction step and the second correction step. The classification result which has been corrected by the first correction step and the second correction step is shown in (b) of FIG. 5. The PP intervals which have been changed by the first correction step and the second correct step are D2, D3 and D6, as shown in (b) of FIG. 5. Based on the P wave periods etc. (waveform intervals) shown in (b) of FIG. 5, the classification correcting section 23 checks characteristics of waveforms W10, W11 and W12 of a waveform data set of a time duration nearby a time on the time axis, where presence of a P wave is estimated. In this example, the classification correcting section 23 determines the waveform W12 as P wave, determines that validity of the classification result of the waveform data set of the time duration including the waveform W12 is low (NO in S4 in FIG. 4), and corrects the classification result (S6). (c) of FIG. 5 illustrates a classification result that the classification of the waveform data set including the waveform W12 has been corrected to "P wave" by the classification correcting section 23.

The classification result in which the correction steps have been performed by the classification correcting section 23 is stored into the memory of the controller 2 or the storage 3. The processing shown in FIGS. 4 and 5 can be performed with respect to another type of waveform than the P wave in a similar manner or the same manner.

According to the physiological information waveform processing apparatus 1 and the method according to the present disclosure, as described above, a waveform of a predetermined time duration can be classified into a predetermined type of waveform by the classification section 22. Further, validity of the classification result is determined by the classification correcting section 23, and the classification result is corrected in accordance with the determined validity. Accordingly, recognition accuracy of a physiological information waveform can be improved.

In addition, a plurality of time duration for acquiring a waveform may be set to at least partially overlap with one another on a time axis. Accordingly, in the time duration overlapping with one another, the waveform can be classified into the predetermined type of waveform using the plurality of time duration. Further, determination of validity of the classification result and correction according to the validity are performed a number of times. In this manner, a resolution can be increased and recognition accuracy of the physiological information waveform can be improved more greatly.

In addition, according to the aforementioned method, when the validity of the classification result is low, the classified waveform is corrected to not the predetermined type of waveform. Next, after the validity of the classification result has been determined again based on the period of the predetermined type of waveform, the classification result is corrected again. In this manner, recognition accuracy of the physiological information waveform can be improved more greatly.

Incidentally, in the aforementioned embodiment, the controller 2 including the acquiring section 21, the classification section 22 and the classification correcting section 23 has been described by way of example. However, the acquiring section 21, the classification section 22 and the classification correcting section 23 are limited to the aforementioned configuration but may be included respectively in separate devices which are configured communicably with one another through the network interface 5.

In addition, in the aforementioned embodiment, the ECG data, the classification result of the classification section 22, the various thresholds or the like about the validity, and the classification result of the classification correcting section 23 are stored into the memory of the controller 2 or the storage 3. However, the ECG data, the classification result of the classification section 22, the various thresholds or the like about the validity, and the classification result of the classification correcting section 23 may be stored into an external device or storage medium with which the controller 2 can communicate through the network interface 5.

In addition, in the aforementioned embodiment, the classification correcting section 23 acquires the thresholds or the criteria from the storage 3 etc. However, the classification correcting section in the present disclosure is not limited to the aforementioned example. For example, the classification correcting section may be constructed based on deep learning of big data using a neural network. In this case, the validity of the classification result may be determined using a characteristic amount through the deep learning.

In addition, in the aforementioned embodiment, the supplementation of an omission of classification which should have been performed by the classification section 22 is executed as the third correction step after the first correction step and the second correction step. However, the supplementation of the classification omission (correction step designated by S6 in FIG. 4) is not limited to the aforementioned example. The supplementation of the classification omission can be also performed when there is no change in the period etc. (waveform interval) due to correction of the classification.

In addition, although the case where P wave, QRS complex and T wave are illustrated as the predetermined type of waveform in the aforementioned embodiment, the predetermined type of waveform is not limited to the aforementioned waveforms. The type of waveform in the present disclosure may include a type etc. indicating a normal heat or premature ventricular contraction (VPC) about the QRS complex of the physiological information waveform.

In addition, the physiological information waveform according to the present disclosure is not limited to the ECG, but can be, for example, of brain waves or pulses.

In addition, in the aforementioned embodiment, an atrioventricular block is determined by the determination section 24. However, the determination of the determination section 24 is not limited to the aforementioned one. When the physiological information waveform is a pulse wave, the determination section 24 can perform various determinations in accordance with the physiological information waveform, such as determination of an arteriosclerotic index.

In addition, in order to realize the physiological information waveform processing apparatus 1 according to the embodiment by software, the physiological information waveform processing program may be installed into the memory of the controller 2, the storage 3 or the ROM in advance. In addition, the physiological information waveform processing program may be stored in a computer-readable storage medium such as a magnetic disk (such as an HDD or a floppy (registered trademark) disk), an optical disk (such as a CD-ROM, a DVD-ROM or a Blu-ray (registered trademark) disk), a magneto-optical disk (such as an MO), or a flash memory (such as an SD card, a USB memory or an SSD). In this case, when the storage medium is connected to the physiological information waveform processing apparatus 1, the physiological information waveform processing program stored in the storage medium can be installed into the memory of the controller 2 or the storage 3. The program which has been installed into the memory of the controller 2 or the storage 3 is loaded onto the RAM, and the processor executes the loaded program. In this manner, the controller 2 executes the various processes shown in FIGS. 3 and 4. In other words, when the program is executed by the processor, the controller 2 functions as the acquiring section 21, the classification section 22, the classification correcting section 23 and the determination section 24 individually. According to the physiological information waveform processing program and the storage medium storing this program, waveform recognition accuracy can be improved.

In addition, the physiological information waveform processing program may be downloaded from the computer on the communication network through the network interface 5. Also in this case, the downloaded program is installed into the memory of the controller 2 or the storage 3 and the controller 2 executes the various processes shown in FIGS. 3 and 4, in a similar manner to or the same manner as the case where the storage medium is connected to the physiological information waveform processing apparatus 1. According to the physiological information waveform processing program, waveform recognition accuracy can be improved.

The present disclosure is not limited to the aforementioned embodiment or modification. However, modification, improvement, etc. can be made on the present disclosure suitably and desirably. In addition, the materials, shapes, forms, numbers, arrangement places, etc. of the respective constituent elements in the aforementioned embodiment are not limited but may be set desirably as long as the present disclosure can be achieved.

This application is based on Japanese Patent Application No. 2017-082921 filed on Apr. 19, 2017, the entire contents of which are incorporated herein by reference.

What is claimed is:

1. A method implemented by a computer, the method comprising:
    acquiring at least one set of waveform data having a time duration from physiological information waveform data;
    classifying a waveform included in the waveform data into a predetermined type of waveform among a plurality of predetermined type of waveforms, based on an interval of the predetermined type of waveform;
    determining validity of a classification result of the waveform based on whether or not a shape of the waveform conforms to the shape of the predetermined type of waveform; and
    correcting the classification result in accordance with the validity of the classification result and applying a different interval of a different type of waveform for re-classification when the validity of the classification result is low.

2. The method according to claim 1, wherein the acquiring of at least one set of waveform data comprises acquiring a plurality of sets of waveform data each having a time duration.

3. The method according to claim 2, wherein a first time duration of a first set of waveform data of the plurality of sets of waveform data at least partially overlaps with a second time duration of a second set of waveform data of the plurality of waveform data.

4. The method according to claim 2, wherein
    the correcting of the classification result comprises correcting the validity of classification result such that the waveform included in the waveform data does not belong to the predetermined type of waveform, when the validity of the classification result is low, and the determining of the validity comprises determining the validity of the classification result again, based on a period of the predetermined type of waveform.

5. The method according to claim 1, wherein the predetermined type of waveform is P waveform.

6. A non-transitory computer-readable storage medium storing a program causing a computer to perform the method according to claim 1.

7. An apparatus comprising:
- at least one processor; and
- at least one memory storing a computer-readable instruction,
- wherein the computer-readable command, when executed by the processor, causes the processor to perform the method according to claim 1.

* * * * *